United States Patent
Itah et al.

(10) Patent No.: US 11,844,616 B2
(45) Date of Patent: Dec. 19, 2023

(54) ENHANCED VISUALIZATION OF ORGAN ELECTRICAL ACTIVITY

(71) Applicant: Biosense Webster (Israel) Ltd., Yokneam (IL)

(72) Inventors: Refael Itah, Tel Aviv (IL); Aharon Turgeman, Zichron Ya'acov (IL); Daniel Melby, North Oaks, MN (US); Gal Hayam, Tivon (IL); Tal Bar-on, Kiryat Tivon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 379 days.

(21) Appl. No.: 16/986,871

(22) Filed: Aug. 6, 2020

(65) Prior Publication Data

US 2021/0045648 A1 Feb. 18, 2021

Related U.S. Application Data

(60) Provisional application No. 62/886,111, filed on Aug. 13, 2019.

(51) Int. Cl.
*A61B 5/287* (2021.01)
*A61B 5/339* (2021.01)
*A61B 5/00* (2006.01)

(52) U.S. Cl.
CPC .............. *A61B 5/287* (2021.01); *A61B 5/339* (2021.01); *A61B 5/6859* (2013.01); *A61B 5/745* (2013.01)

(58) Field of Classification Search
None
See application file for complete search history.

(56) References Cited

U.S. PATENT DOCUMENTS 8,340,766 B2 * 12/2012 Ryu ................ A61B 5/361
607/9
8,359,092 B2 * 1/2013 Hayam ............ A61B 5/341
600/509

(Continued)

FOREIGN PATENT DOCUMENTS

WO WO2018106496 A1 6/2018

OTHER PUBLICATIONS

Linton, Nick W F et al. "Cardiac ripple mapping: a novel three-dimensional visualization method for use with electroanatomic mapping of cardiac arrhythmias." pp. 1754-1762, Heart rhythm vol. 6,12 (2009).

(Continued)

*Primary Examiner* — Carl H Layno
*Assistant Examiner* — Manolis Pahakis
(74) *Attorney, Agent, or Firm* — Volpe Koenig

(57) ABSTRACT

Methods, apparatus, and systems for medical procedures are disclosed herein and include sensing a plurality of tissue electrical potentials at an organ area of an organ, by one or more electrodes on a catheter, determining a number of peak electrical potentials from the plurality of first tissue electrical potentials such that the a peak electrical potential exceeds a potential threshold, determining a first visual characteristic based on the number of peak electrical potential and displaying a rendering of the organ comprising the organ area such that the rendering of the first organ area comprises the first visual characteristic.

20 Claims, 13 Drawing Sheets

(56) References Cited

U.S. PATENT DOCUMENTS

| | | | | |
|---|---|---|---|---|
| 8,965,496 | B2* | 2/2015 | Bailin | A61B 5/7203 |
| | | | | 600/443 |
| 9,456,759 | B2* | 10/2016 | Lian | A61B 5/316 |
| 9,538,929 | B2* | 1/2017 | Yang | A61B 5/0044 |
| 9,788,751 | B2* | 10/2017 | Li | A61B 5/0538 |
| 9,990,470 | B2* | 6/2018 | Yang | G16Z 99/00 |
| 10,617,317 | B2* | 4/2020 | Cohen | A61B 5/339 |
| 2002/0065459 | A1 | 5/2002 | Macadam et al. | |
| 2007/0073179 | A1* | 3/2007 | Afonso | A61B 5/316 |
| | | | | 600/523 |
| 2007/0197929 | A1* | 8/2007 | Porath | A61B 5/349 |
| | | | | 600/509 |
| 2007/0208260 | A1* | 9/2007 | Afonso | A61B 5/287 |
| | | | | 600/300 |
| 2008/0009758 | A1* | 1/2008 | Voth | A61B 5/318 |
| | | | | 600/523 |
| 2008/0188765 | A1* | 8/2008 | Stolarski | A61B 5/363 |
| | | | | 600/518 |
| 2009/0076476 | A1* | 3/2009 | Barbagli | A61B 5/1076 |
| | | | | 600/587 |
| 2010/0004550 | A1* | 1/2010 | Ishay | A61B 5/283 |
| | | | | 600/515 |
| 2010/0274123 | A1* | 10/2010 | Voth | A61B 5/283 |
| | | | | 382/128 |
| 2013/0253349 | A1* | 9/2013 | Hayam | A61B 5/361 |
| | | | | 600/509 |
| 2014/0031708 | A1* | 1/2014 | Lo | A61B 5/7282 |
| | | | | 600/518 |
| 2014/0235988 | A1* | 8/2014 | Ghosh | A61B 18/1492 |
| | | | | 600/374 |
| 2016/0022375 | A1 | 1/2016 | Blake et al. | |
| 2018/0116539 | A1 | 5/2018 | Olson et al. | |
| 2019/0200886 | A1 | 7/2019 | Welsh | |
| 2020/0397327 | A1* | 12/2020 | Stewart | A61B 5/349 |

OTHER PUBLICATIONS

"Carto 3—Further Efficiency in Mapping All Your Complex Arrhythmias," Johnson & Johnson Medical NV/SA (2018). Available at: https://www.radcliffecardiology.com/gallery/carto-3-further-efficiency-mapping-all-your-complex-arrhythmias.

Extended European Search Report dated Dec. 14, 2020 for European Patent Application No. 20191016.3.

* cited by examiner

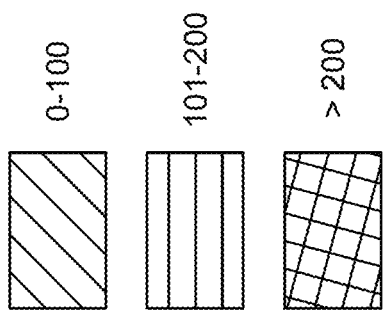
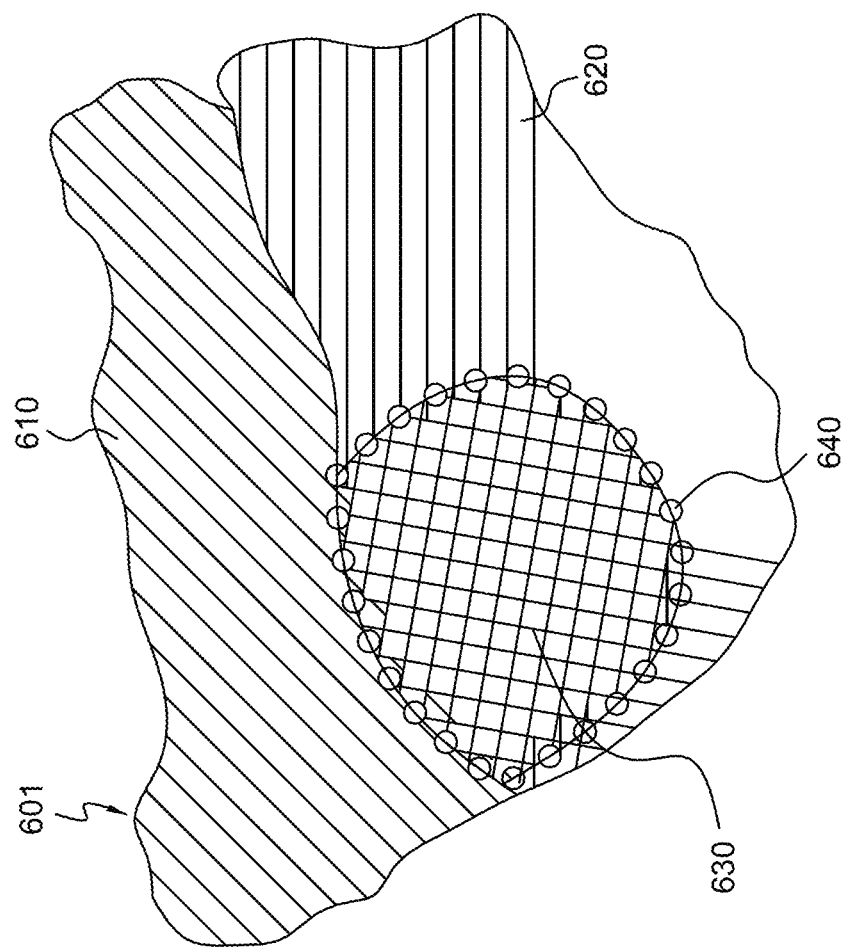
FIG. 6

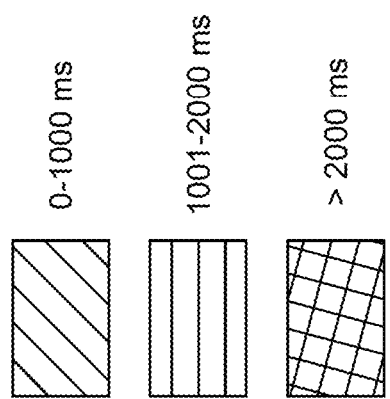
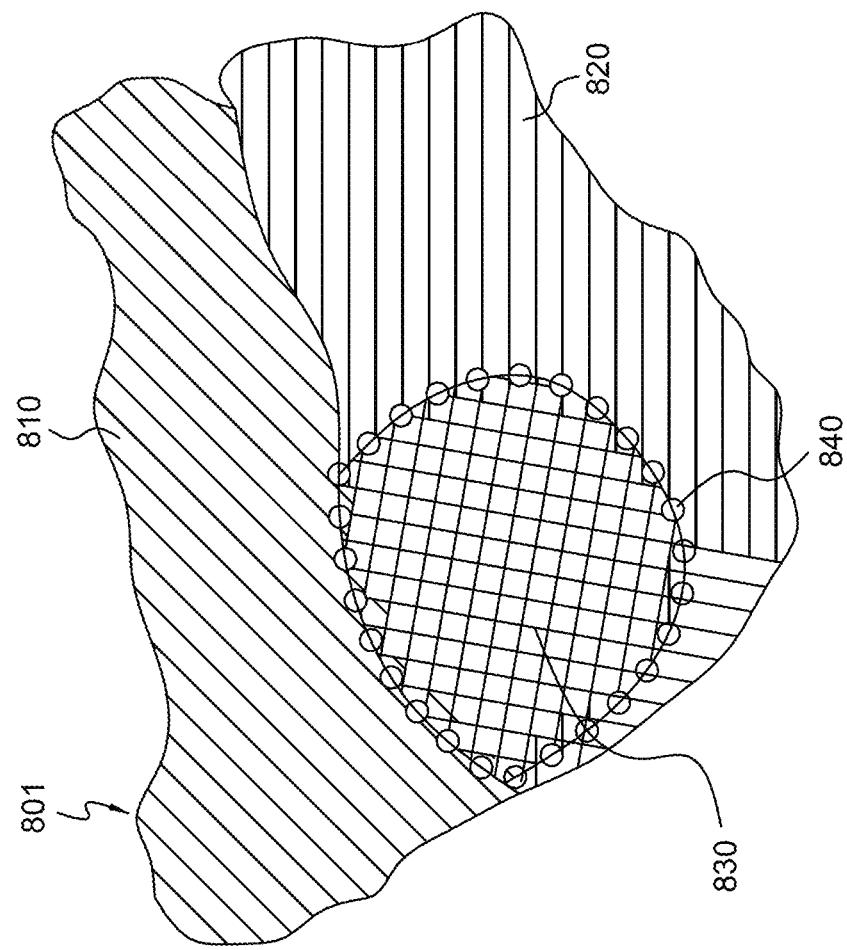
FIG. 8

ENHANCED VISUALIZATION OF ORGAN ELECTRICAL ACTIVITY

CROSS-REFERENCE TO RELATED APPLICATIONS

This application claims priority to U.S. provisional application Ser. No. 62/886,111 filed on Aug. 13, 2019.

FIELD OF INVENTION

The present application provides systems, apparatuses, and methods for improving cardiac procedures.

BACKGROUND

Cardiac ablation is a surgical procedure that treats abnormal heart rhythms of a patient by scaring or destroying the tissue in the patient's heart that is responsible for the abnormal rhythms. Cardiac ablation is often used to treat cardiac arrhythmias such as atrial fibrillation, atrial flutter, supraventricular tachycardias, and Wolff-Parkinson-White syndrome. In the cardiac ablation procedure, electrical measurements of the heart are made using catheters. Then, based on the measurements, the surgeon uses heat (radiofrequency), extreme cold (cryoablation), or lasers to scar or destroy the areas of the heart where the electrical anomaly is believed to be occurring.

Traditional cardiac ablation procedures have relied solely on the subjective skill of the surgeon to determine where and how to perform the ablation. The traditional methods have resulted in high variability in clinical outcomes from patient to patient, surgeon to surgeon and hospital to hospital

SUMMARY

Methods, apparatus, and systems for medical procedures are disclosed herein and include sensing a plurality of tissue electrical potentials at an organ area of an organ, by one or more electrodes on a catheter, determining a number of peak electrical potentials from the plurality of first tissue electrical potentials such that the peak electrical potential exceeds a potential threshold, determining a first visual characteristic based on the number of peak electrical potentials and displaying a rendering of the organ comprising the organ area such that the rendering of the first organ area comprises the first visual characteristic.

BRIEF DESCRIPTION OF THE DRAWINGS

A more detailed understanding can be had from the following description, given by way of example in conjunction with the accompanying drawings wherein:

FIG. 6 is a diagram of a heart with visual characteristics based on electrical potentials of a heart, in accordance with an embodiment of the disclosed subject matter;

FIG. 8 is a diagram of a heart with visual characteristics for electrical potential activity based on time, in accordance with an embodiment of the disclosed subject matter;

DETAILED DESCRIPTION

According to implementations of the disclosed subject matter, a rendering of an organ, such as a heart, may be provided such that the rendering includes visual characteristics based on electrical potentials at different areas of the organ. By providing visual characteristics based on electrical potentials, an area of the organ with outlier electrical potentials may easily be identified as an area for ablation. Accordingly, as further disclosed herein, a static rendering of an organ with such visual characteristics based on electrical potentials is provided.

Figure 1:
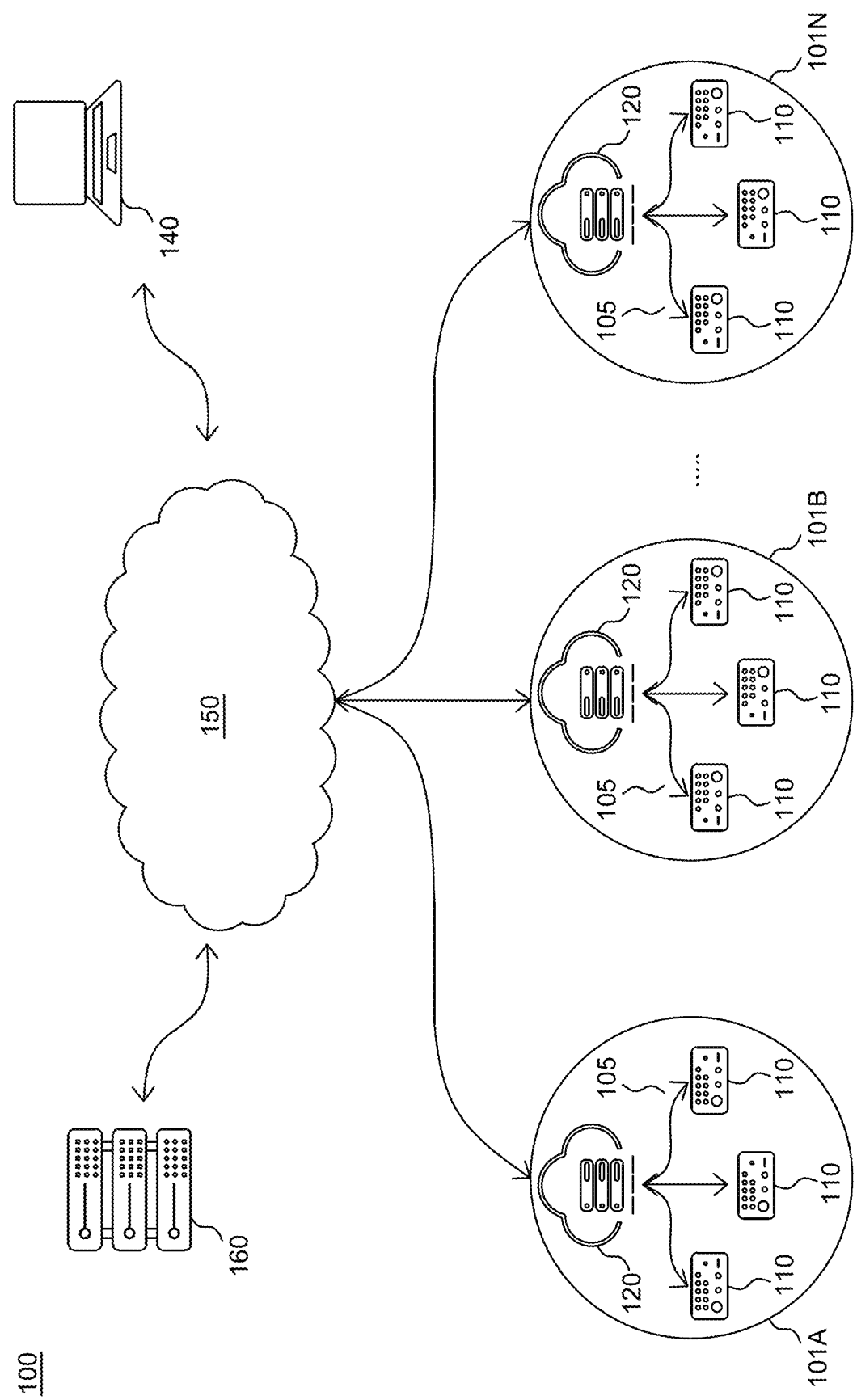
FIG. 1 is a diagram of an exemplary system in which one or more features of the disclosure subject matter can be implemented.

FIG. 1 is a diagram of an exemplary system 100 in which one or more features of the disclosure can be implemented. In system 100, a plurality of discrete surgical networks 101A-101N are connected to a cloud platform 160 by a network 150. In some instances, the cloud platform 160 is implemented by a public cloud computing platform (such as Amazon Web Services, or Microsoft Azure), a hybrid cloud computing platform (such as HP Enterprise OneSphere) or private cloud computing platform.

The discrete surgical networks 101A-101N may be located at separate hospitals or in separate healthcare provider networks. Each of the discrete surgical networks 101 includes one or more surgical systems 110 connected to a local server 120. The one or more surgical systems are capable of obtaining anatomical and electrical measurements of a patient's organ, such as a heart, and performing a cardiac ablation procedure. An example of a surgical system 110 that may be used in system 100 is the Carto® system sold by Biosense Webster. In some instances, the surgical system 110 may also associate the measurements with a unique patient identification (ID) or other information that can be used to uniquely identify the patient.

The surgical system 110 may also, and optionally, obtain anatomical measurements of the patient's heart using ultrasound, computed tomography (CT), magnetic resonance imaging (MRI) or other medical imaging techniques known in the art. The surgical system 110 may obtain electrical measurements using catheters, electrocardiograms (EKGs) or other sensors that measure electrical properties of the heart. The anatomical and electrical measurements may then be stored in a local memory of the surgical system 110 and transmitted to the local server 120 using the private network 105. In some instances, the electrical and anatomical measurements are transmitted to local server 120 immediately on acquisition.

Figure 2A:
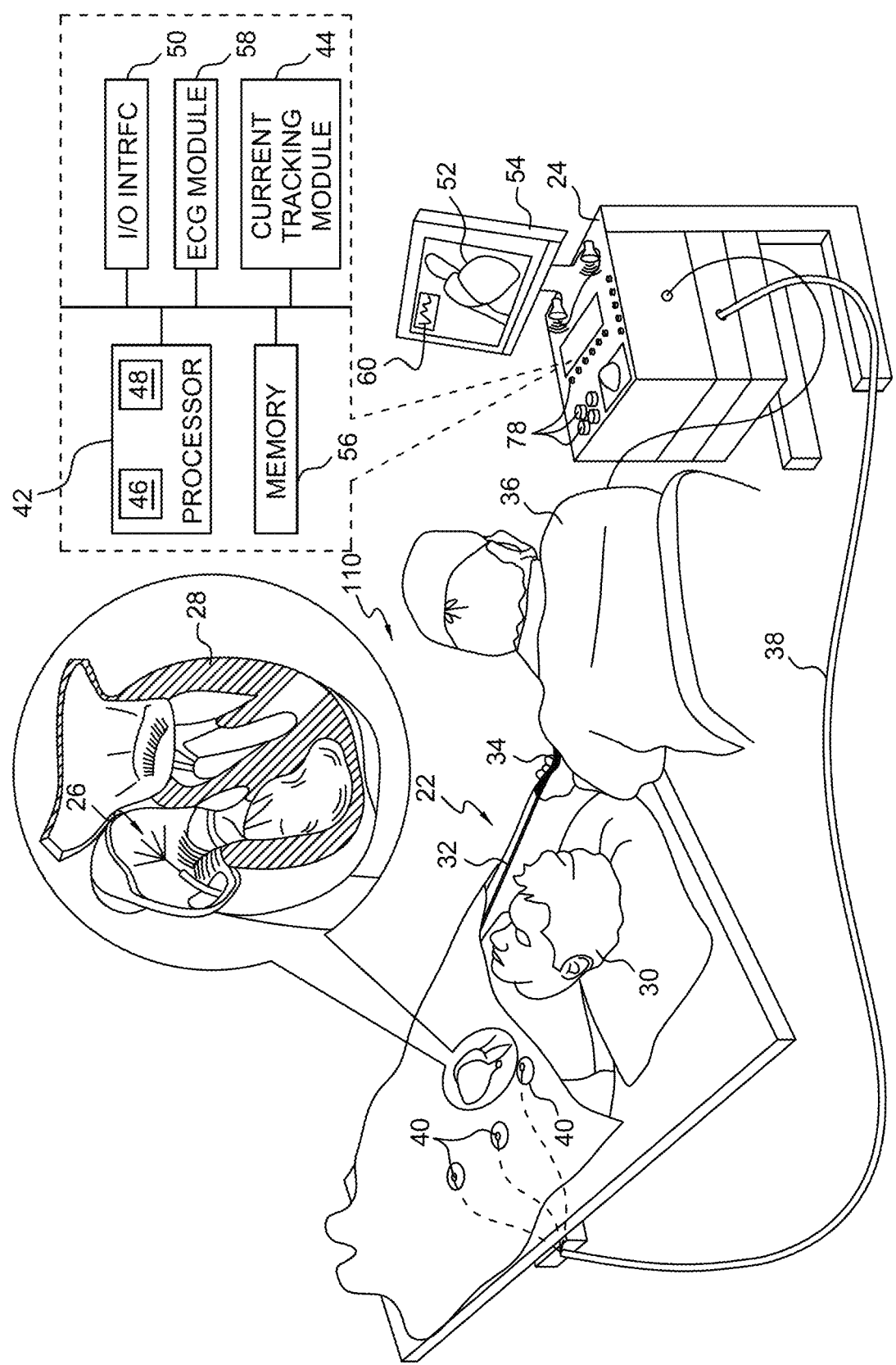
FIGS. 2A and 2B are illustrations of a medical system comprising a mapping catheter, in accordance with an embodiment of the disclosed subject matter.

The surgical system 110 then generates mappings of the patient's heart by combing the electrical and anatomical measurements. The mappings of the patient's heart may be stored in the local memory (e.g., memory 56, as shown in FIG. 2A) of the surgical system 110 and transmitted to the local server 120 using the private network 105. In some instances, the mappings may be transmitted to local server 120 immediately on generation.

The surgical system 110 enables the surgeon to perform a cardiac ablation procedure. In some instances, the cardiac ablation procedure may utilize contact force technology and irrigated ablation technology. An ablation procedure may be performed in accordance with the techniques disclosed herein and may include identifying ablation areas based on visual characteristics of a static map.

Private network 105 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the surgical systems 110 and the local server 120. The network 105 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 105.

The local server 120 receives the electrical and anatomical measurements, the mappings and the information regarding the ablation procedure in a local database. In some instances, the local database associates the data received with unique patent identifiable information.

In some instances, the local server 120 is implemented as a physical server. In other instances, the local server 120 is implemented as a virtual server a public cloud computing provider (e.g., Amazon Web Services (AWS)®).

In some instances, the local server 120 uses machine learning or other artificial intelligence techniques to analyze the data stored in the local database. Such data may be associated with electrical potentials above a potential threshold or shapes of scar areas, as further disclosed herein. The local server may use machine learning to: 1) consider all of the prior patents having similar cardiac conditions and morphologies and the associated ablation procedure data and best outcomes from prior patients in order to recommend optimal treatment plans for a cardiac ablation to be performed; 2) modify a treatment plan or threshold while the cardiac ablation is about to be or is being performed and make specific recommendations to a physician during the ablation procedure, considering the aforementioned prior patient and ablation data; and/or 3) to evaluate the performance of the surgeon that performed the cardiac ablation in view of the treatment plan and the outcome of the patient. In this manner, a physician has the accumulated experience of all prior patients and cardiac procedures at their disposal in planning, treating and evaluating an ablation procedure in order to achieve the best patient outcomes.

Collection and analysis of data regarding a specific procedure may include statistics on the procedure and are available by respective patients, broken down by specific and separate portions of the procedure. This will help physicians and researchers measure the effect of any parameter over any other parameter. In one example, collection and analysis of such data will enable researchers to evaluate any changes that are introduced into the cardiac catheter procedure, for example, a potential threshold, a visual characteristic, and the like. This will allow researchers to determine if these changes improve patient outcomes.

Public network 150 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between the discrete surgical networks 101A-101N and the cloud-based platform 160. The public network 150 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 150.

The cloud-based platform 160 may receive data from each local server 120 of the discrete surgical networks 101A-101N and stores the received information in a database. In many instances, the cloud-based platform 160 also provides a portal for third parties 140 to query the data stored in the database via the network 150. In some instances, the third party 140 may use a standard internet browser to access the portal of the cloud-based platform 160. In other instances, a dedicated application is required for the third party 140 to access the portal of the cloud-based platform 160.

Figure 2B:
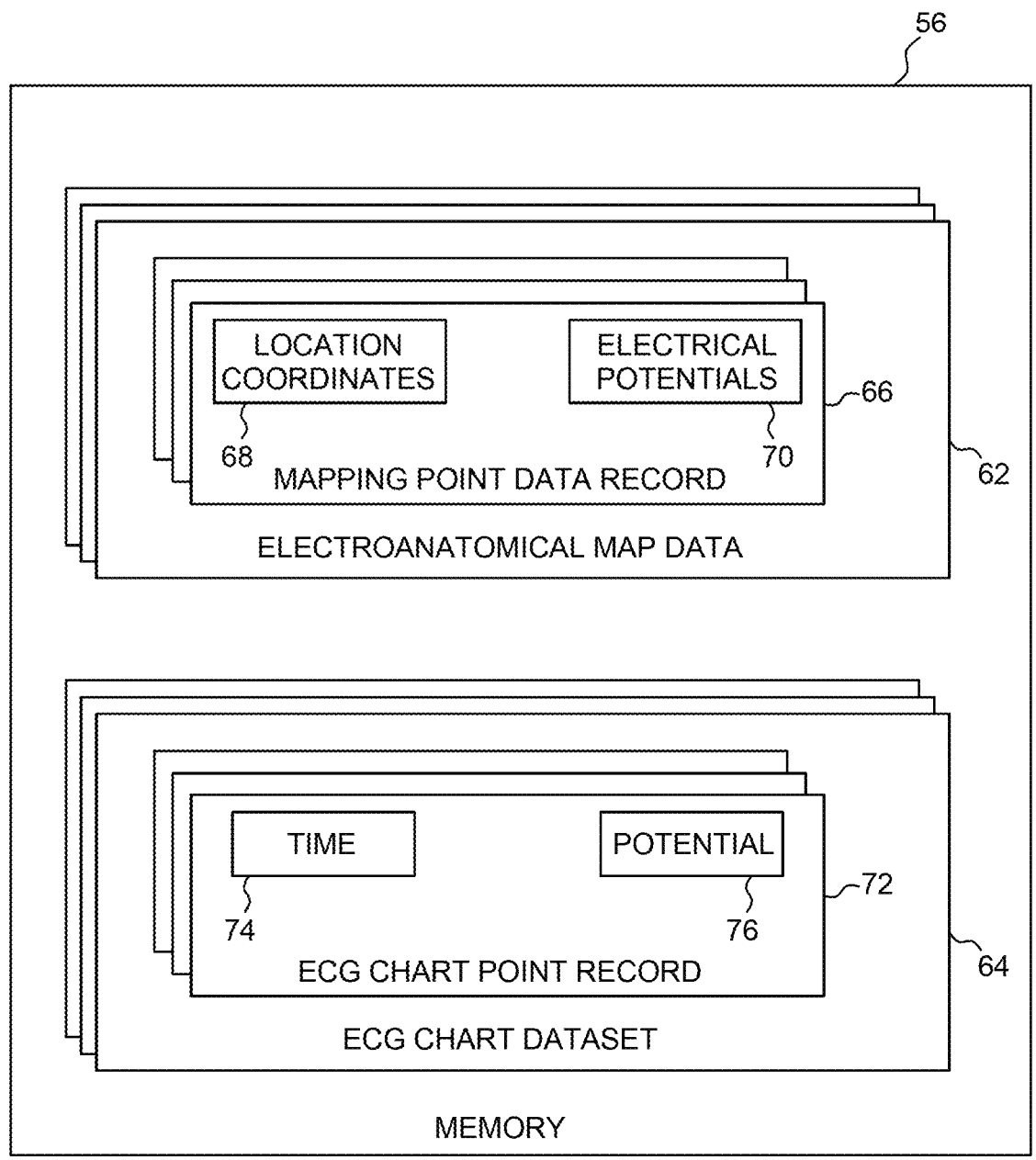
Figure 3:
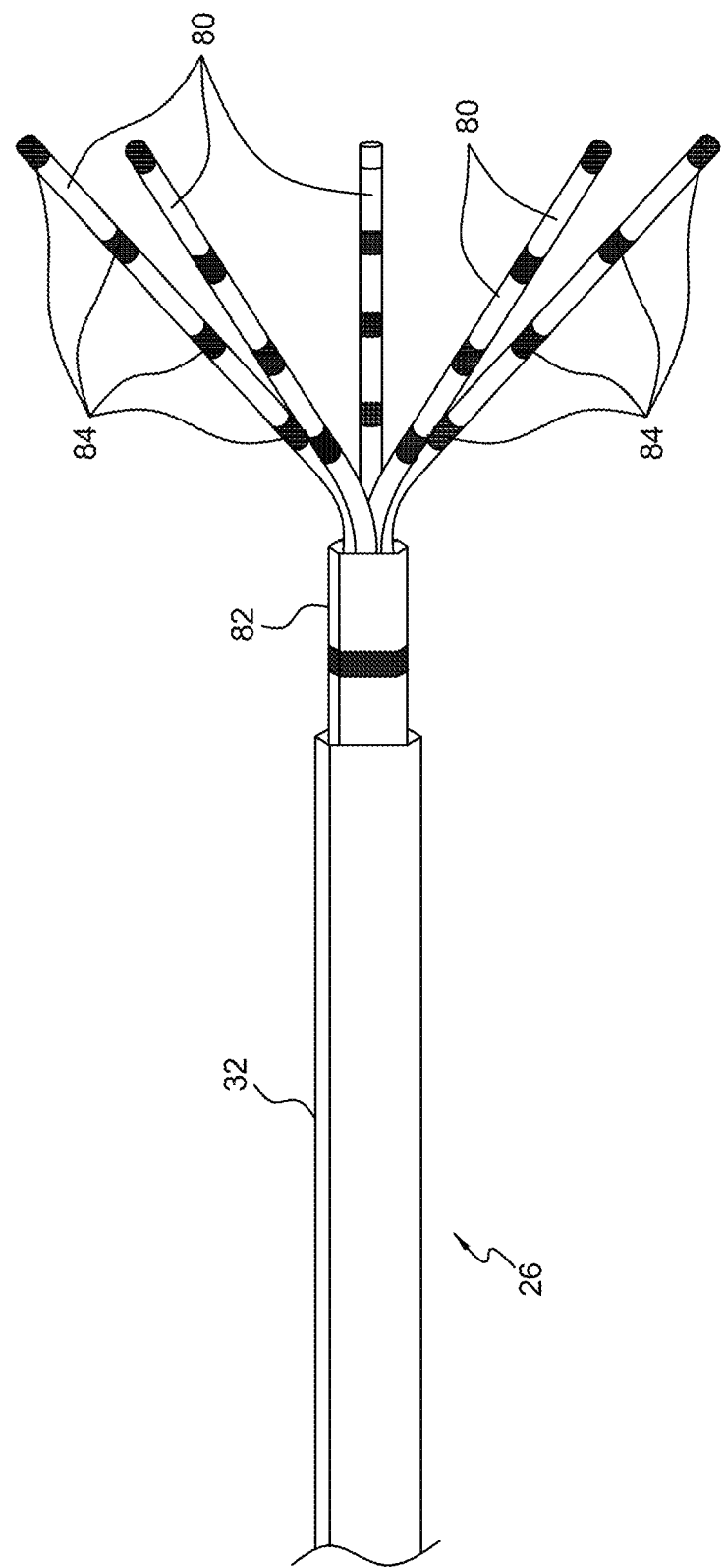
FIG. 3 is an illustration of a distal end of the mapping catheter, in accordance with an embodiment of the disclosed subject matter.

FIGS. 2A and 2B are illustrations of a surgical system 110 comprising a medical probe 22 and a control console 24, and FIG. 3 is an illustration of a distal end 26 of the medical probe 22, in accordance with an embodiment of the present invention. Surgical system 110 may be a part of the system 100, as shown in FIG. 1. In embodiments described hereinbelow, medical probe 22 can be used for diagnostic or therapeutic treatment, such as for mapping electrical potentials of a heart 28 of a patient 30. In embodiments described herein, medical probe 22 may also be referred to as a mapping catheter and/or ablation catheter. Alternatively, medical probe 22 may be used for other therapeutic and/or diagnostic purposes in the heart or in other body organs.

Medical probe 22 comprises an insertion tube 32 and a handle 34 coupled to a proximal end of the insertion tube. By manipulating handle 34, a medical professional 36 can insert medical probe 22 into a body cavity in patient 30. For example, medical professional 36 can insert medical probe 22 through the vascular system of patient 30 so that distal end 26 of medical probe 22 enters a chamber of heart 28 and engages myocardial tissue at a desired location or locations. By way of example, as shown in FIG. 3, distal end 26 of medical probe 22 comprises flexible splines 80 that are formed at the end of a tubular shaft 82. During a medical procedure, medical professional 36 can deploy splines 80 by extending tubular shaft from insertion tube 32.

Control console 24 is connected, by a cable 38, to body surface electrodes, which typically comprise adhesive skin patches 40 that are affixed to the patient 30. Control console 24 comprises a processor 42 that, in conjunction with a current tracking module 44, determines position coordinates of the distal end 26 of the probe 22 inside the heart 28 based on impedances measured between the adhesive skin patches 40 and electrodes 84 that are affixed to splines 80 as shown in FIG. 3. In embodiments described herein, electrodes 84 can also be configured to apply a signal to tissue in the heart 28, and/or to measure a certain physiological property (e.g., the local surface electrical potential) at a location in the heart. Electrodes 84 are connected to control console 24 by wires (not shown) running through medical probe 22.

While embodiments herein show medical probe 22 comprising a multi-spline intracardiac catheter, using other multi-electrode intracardiac catheters or single electrode catheters are considered to be within the scope of the present disclosure.

Processor 42 may comprise real-time noise reduction circuitry 46 typically configured as a field programmable gate array (FPGA), followed by an analog-to-digital (A/D) ECG (electrocardiograph) or EMG (electromyogram) signal conversion integrated circuit 48. The processor can pass the signal from A/D ECG or EMG circuit 48 to another processor and/or can be programmed to perform one or more algorithms disclosed herein, each of the one or more algorithms comprising steps described hereinbelow. The processor uses noise reduction circuitry 46 and signal converting integrated circuit 48, as well as features of modules which are described in more detail below, in order to perform the one or more algorithms.

The surgical system shown in FIG. 1 and FIGS. 2A and 2B may use impedance-based sensing to measure a location of the distal end 26 of probe 22; however, other position tracking techniques may be used (e.g., techniques using magnetic-based sensors).

Control console 24 also comprises an input/output (I/O) communications interface 50 that enables the control console to transfer signals from, and/or transfer signals to electrodes 84 and adhesive skin patches 40. Based on signals received from electrodes 84 and/or adhesive skin patches 40, processor 42 can generate an electrical potential based map 52 (FIG. 2A) that shows electrical potential based visual characteristics, as disclosed herein.

During a procedure, processor 42 can present an electrical potential based map 52 to medical professional 36 on a display 54, and store data representing the electrical potential based map 52 in a memory 56, as described in the description referencing FIG. 2A hereinbelow. Memory 56 may comprise any suitable volatile and/or non-volatile memory, such as random-access memory or a hard disk drive. In some embodiments, medical professional 36 can manipulate map 52 using one or more input devices 78. In alternative embodiments, display 54 may comprise a touchscreen that can be configured to accept inputs from medical professional 36, in addition to presenting electrical potential based map 52.

Control console 24 may also comprise an electromyogram (EMG) module 58 that can be configured to generate an EMG chart 60 from the signals received from electrodes 84. In some embodiments, processor 42 presents one or more EMG charts 60 on display 54 (i.e., along with LAT map 52), and store data representing the EMG chart map in memory 56.

As shown in FIG. 2B, memory 56 stores electroanatomical map data 62 that processor 42 can use to generate and render electroanatomical map 52, and stores EGM chart datasets 64 that the processor can use to generate and render EGM charts 60. Electroanatomical map data comprises a plurality of mapping point records 66, each of the mapping point records comprising a set of location coordinates 68 (i.e., in patient 30) and electrical potentials 70. In embodiments herein location coordinates 68 may also be referred to as locations 68.

Each EGM signal dataset 64 comprises multiple EGM chart point records 72, each of the EGM signal point records comprising a measurement time 74 and an electrical potential measurement 76. In embodiments herein, each given electrode 84 has a corresponding one-to-one correspondence with a given EGM chart dataset 64. In other words, each given EGM chart dataset 64 stores multiple EGM chart point records which in turn stores electrical potential measurements 76 and measurement times 74 that processor 42 receives from its corresponding electrode 84.

Figure 4:
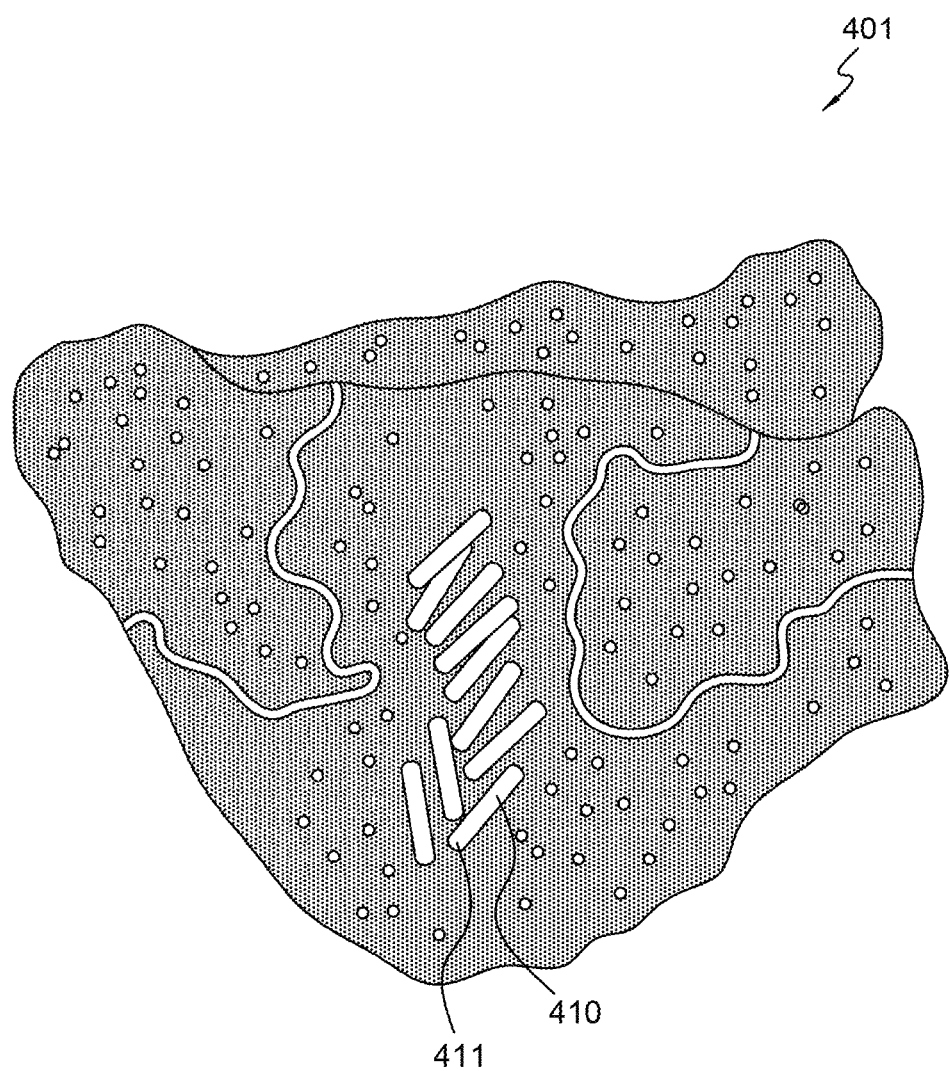
FIG. 4 is a diagram of a heart with electrical potential bars, in accordance with an embodiment of the disclosed subject matter.

FIG. 4 shows a rendering of an organ 401 which may be similar to the heart 28 of FIG. 2A. The organ 401 may be mapped using a surgical system, such as surgical system 110 of FIG. 1 and FIGS. 2A and 2B by using a medical probe 22. Medical probe 22 may traverse different areas of the organ and may use contact, tissue proximity, and/or electrical potentials or ultrasound signals to determine the shape and boundaries of the organ 401.

A medical probe 22 that includes one or more electrodes may be used to sense tissue electrical potentials at different areas of an organ. The tissue electrical potentials may be sensed when the medical probe 22 is in contact with tissue of an organ area or may be sensed when the medical probe 22 is in proximity to tissue of an organ area. One or more electrodes on the medical probe 22 may sense the electrical potential of an organ area based on electron flow/change in voltage at the organ area. An organ area may be a physical point where a medical probe 22 senses electrical potentials. Accordingly, an organ may have as many organ areas as the unique number of points where medical probe 22 senses electrical potentials. The one or more electrodes on the medical probe 22 may provide the sensed signals to one or more components of the system 100 of FIG. 1 such as via a discrete surgical network 101A-101N, network 150, and/or cloud platform 160.

FIG. 4 shows visual indications of electrical potential activity, including electrical potential 410, as raised bars, on the surface of organ 401. As shown, electrical potential 410 corresponds to organ area 411 such that the electrical potential 410 is the electrical potential sensed by medical probe 22 when it is in contact with or proximate to the organ area 411.

The visual indication of electrical potential 410 for organ area 411 is shown as an absolute value in FIG. 4. FIG. 4 shows an example number of electrical potentials such as electrical potential 410 at a given time or over a range of time. The electrical potentials, including electrical potential 410, may be sensed by one or more catheter such as medical probe 22 of FIG. 3. The electrical potential 410 is a visual indication, as a bar, of the amplitude of the electrical potential at the organ area 411. The other electrical potentials shown in FIG. 4 are, similarly, visual indications, as bars, of the amplitude of electrical potentials at different organ areas. Alternatively, the visual indications, such as electrical potential 410, may correspond to an electrical potential at a given area (e.g., organ area 411) reaching a threshold electrical potential. As further disclosed in reference to FIG. 5, multiple electrical potentials may be collected over a given period of time and an organ area, such as the organ area 411 of FIG. 4, may be rendered using a visual characteristic determined based on the number of electrical potentials in that organ area that exceed a given threshold electrical potential. As further disclosed in reference to FIG. 7, multiple electrical potentials may be collected over a given period of time and an organ area, such as the organ area 411 of FIG. 4 may be rendered using a visual characteristic based on the amount of time that electrical potentials in that organ area exceed a threshold electrical potential.

Figure 5:
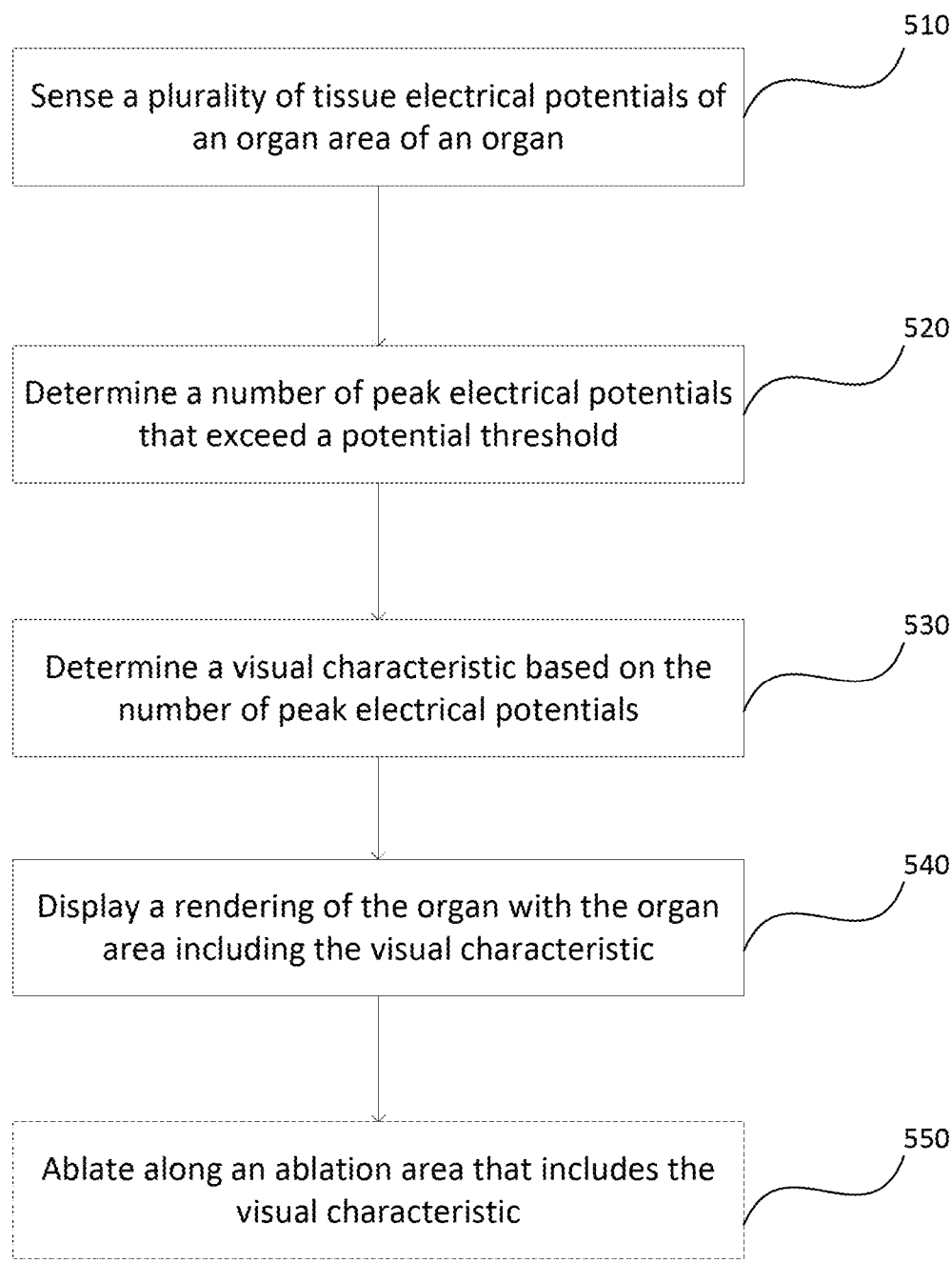
FIG. 5 is a flowchart for visualizing the amount of electrical potential activity, in accordance with an embodiment of the disclosed subject matter.

FIG. 5 shows a flowchart 500 for visualizing an amount of electrical potential activity, such as the electrical potential activity shown in FIG. 4. At step 510, a plurality of tissue electrical potentials of each of a plurality of organ areas are sensed. The plurality of electrical potentials at each organ area may be sensed using a medical probe, such as medical probe 22 of FIG. 2A. The plurality of electrical potentials may be sensed by one or more electrodes of the medical probe as the medical probe traverses different organ areas of an organ, such as organ 401 of FIG. 4.

The number of electrical potentials per organ area, sensed by a medical probe, may be pre-determined. According to an implementation, the number of electrical potentials per organ area may be in the range of 2000 and 3000 electrical potentials, for example, 2500 electrical potentials per organ area. According to an exemplary implementation, the medical probe may sense the pre-determined number of electrical potentials per organ area starting when the medical probe is in contact with or proximate to the tissue of the organ area. Alternatively, the medial probe may sense the pre-determined number of electrical potentials per organ area after an amount of time, such as an amount of time allocated for the medical probe to stabilize.

According to another exemplary implementation, the medical probe may sense a number of electrical potentials for each organ area for a given amount of time. The medical probe may be configured to sense electrical potentials at a pre-determined or provided frequency. For example, the medical probe may sense electrical potentials at the rate of approximately 1 electrical potential per millisecond. Accordingly, the medical probe may sense electrical potentials of an organ area for a predetermined or provided amount of time such that the number of electrical potentials that are sensed and/or stored, for each organ area, are approximately the same. It will be understood that a sub-set of an overall number of electrical potentials, for an organ area, may be stored and/or applied in subsequent step 520 of the process illustrated in FIG. 5, as further described herein.

As an example, medical probe 22 of FIG. 2A may be in contact with organ area 411 of FIG. 4. The medical probe 22 may sense the electrical potentials at organ area 411 for a sum of 2.5 seconds and at a frequency of 1 sensed electrical potential per millisecond. Accordingly, the medical probe 22 may sense a total of 2500 electrical potentials for the organ area 411.

At step 520 of the process illustrated in FIG. 5, a number of peak electrical potentials, from the sensed electrical potentials, that exceed a potential threshold, may be determined. According to an implementation, a potential threshold may be minimum electrical potential value such that electrical potentials sensed by the medial probe that are below the minimum electrical potential may not be included when determining the number of peak electrical potentials. For example, the potential threshold may be 0.05 mV such that any sensed electrical potentials that do not meet or exceed 0.05 mV may not be included when determining the number of peak electrical potentials. It will be understood that a peak electrical potential may be any electrical potential, whether positive or negative, that exceeds the potential threshold. According to an implementation, an absolute value of the electrical potential may be used when determining peak electrical potentials.

According to an implementation, a potential threshold may be a pre-determined potential value. A pre-determined potential may be stored in memory, such as memory 56 of FIG. 2A, and/or may be provided to a processor, such as processor 42 of FIG. 2A. The processor 42 may determine the number of peak electrical potentials, from the sensed electrical potentials, that exceed the potential threshold.

According to another exemplary implementation, a potential threshold may be determined based on an analysis of the electrical potentials sensed for the organ and may vary from one organ to another and/or from one individual to another. According to this implementation, the processor 42 may analyze the electrical potentials from different organ areas and, based on the analysis, may determine a potential threshold. The processor 42 may determine the potential threshold based on factors including, but not limited to, mean electrical potentials, average electrical potentials, a standard deviation or other distribution, etc.

As an example of step 520 of the process illustrated in FIG. 5, medical probe 22 of FIG. 2A may be in contact with the organ area 411 of FIG. 4 and may collect 2500 electrical potentials over 2.5 seconds. The potential threshold may be set to 0.05 mV and at step 520, of FIG. 5, it may be determined that the 1500 electrical potentials of the 2500 sensed electrical potentials meet or exceed the potential threshold of 0.05 mV. Accordingly, the number of peak electrical potentials for the organ area 411 would be 1500.

At step 530 of the process illustrated in FIG. 5, a visual characteristic, for an organ area, may be determined based on the number of peak electrical potentials for that organ area, as determined at step 520. A visual characteristic may be a color, a texture, a pattern, a gradient, an indicator, a graphic, or the like. As further disclosed herein, the visual characteristic may correspond to the way in which the organ area is rendered and/or displayed.

A visual characteristic may be determined based on the number of peak electrical potentials for an organ area such that a visual characteristic that corresponds to the determined number of peak electrical potentials may be selected from a plurality of visual characteristics. A number of different visual characteristics may be available such that a specific visual characteristic may be determined to be applicable to a specific organ area, based on that organ area's number of peak electrical potentials. According to an implementation, each or a subset of available visual characteristics (e.g., colors) may correspond to a range of number of peak electrical potentials. As an example, the color red may correspond to an organ area with less than 50 peak electrical potentials; the color yellow may correspond to an organ area with 50-100 peak electrical potentials; the color green may correspond to an organ area with 100-150 peak electrical potentials; the color blue may correspond to an organ area with 150-200 peak electrical potentials; and the color purple may correspond to an organ area with 200 or more electrical potentials. It will be understood that the colors described herein may be different or reversed based on a given implementation.

According to an exemplary implementation, different categories of visual characteristics may correspond to different organ areas. For example, a first organ area may correspond to a color based visual characteristic whereas a second organ area may correspond to a pattern based visual characteristic.

At step 540 of the process illustrated in FIG. 5, a rendering of an organ that includes one or more organ areas may be displayed such that each organ area is rendered using its corresponding visual characteristic, as determined at step 530 of the process illustrated in FIG. 5. Accordingly, organ areas with the same or similar number of peak electrical potentials that exceed the potential threshold may be rendered with the same or similar visual characteristic (e.g., may be the same color). Further, it may also be probable that different organ areas that are proximate to each other may have a similar number of peak electrical potentials that exceed the potential threshold and, thus, may be rendered similarly. For example, 30 different organ areas that are proximate to each other may have less than 50 peak electrical potentials that exceed the potential threshold. Accordingly, this number of organ areas may all be rendered as red.

Rendering an organ with one or more organ areas using their corresponding visual characteristics provides a static map of electrical potential activity of the organ. The static map of the organ visually provides an overview of the electrical activity at the organ areas based on the number of electrical potentials that exceed a potential threshold, for each organ area. Such an overview of electrical activity can help identify areas of high electrical activity and low electrical activity.

Organ areas of an organ, as disclosed herein, are points where a medical probe senses electrical potentials. Accordingly, an organ area may be considered a discrete point of an organ. It should be noted that the visual characteristic of an organ area may be applied to a surface area that is larger than the organ area itself. The surface area for the application of a visual characteristic includes the organ area and may extend further based on the proximity of the given organ area to its neighboring organ areas. For example, the surface area for the application of a visual characteristic of a given organ area may be smaller if the organ area is in an area densely surrounded by other organ areas and may be larger if the organ area is not surrounded by other organ areas. For example, a first organ area with a red visual characteristic may be 5 mm away from a second organ area with a purple visual characteristic. According to a simplified example, the organ may be rendered such that the surface area from the first organ area and for 2.5 mm towards the second organ area is red and the surface area from the second organ area and for 2.5 towards the first organ area is purple. Similarly, for example, a first organ area with a red visual characteristic may be 1 mm away from a second organ area with a purple visual characteristic. According to a simplified example, the organ may be rendered such that the surface area from the first organ area for 0.5 mm towards the second organ area is red and the surface area from the second organ area for 0.5 towards the first organ area is purple. It will be understood that although only two organ areas are exemplified for simplicity, multiple adjacent or proximate organ areas may contribute to the determination of an applicable visual characteristic surface area for a given organ area.

Referring now to FIG. 6 there is a rendering of a heart 601 with pattern visual characteristics based on the number of peak electrical potentials of a plurality of organ areas, in accordance with step 540 of the process illustrated in FIG. 5. The organ areas towards the top of the heart 601, as it is visually oriented in FIG. 6, have between 0 and 100 peak electrical potentials. This area is indicated as area 610. Accordingly, area 610 of the heart 601 is rendered with a diagonal line pattern which corresponds to peak electrical potentials of between 0 and 100. It should be noted that area 610 may include one or a number of organ areas, as disclosed herein, which exhibited electrical potentials in the range of 0-100. The organ areas towards the bottom of the heart 601, as it is visually oriented in FIG. 6, have between 101 and 200 peak electrical potentials. This area is indicated as area 620. Accordingly, area 620 of the heart 601 is rendered with a horizontal line pattern which corresponds to peak electrical potentials of between 101 and 200. It should be noted that area 620 may include one or a number of organ areas, as disclosed herein, which exhibited electrical potentials in the range of 101 and 200. The organ areas towards the center of the heart 601, as it is visually oriented in FIG. 6, have over 200 peak electrical potentials. This area is indicated as area 630. Accordingly, area 630 of the heart 601 is rendered with a horizontal line pattern which corresponds to over 200 peak electrical potentials. It should be noted that area 630 may include one or a number of organ areas, as disclosed herein, which exhibited over 200 electrical potentials. It will be understood that, although the disclosure provided herein describes assigning a visual characteristic based on a range, visual characteristics may be assigned or determined based on a gradient, an absolute number, or other iterations that are not necessarily broken up by ranges.

Although a number of peak electrical potentials over a potential threshold for a given organ area are disclosed herein, it should be understood that if the total number of electrical potentials collected for each organ area are not the same, then one or more number of peak electrical potentials over a potential threshold may be normalized. For example, if 100 total electrical potentials are sensed for a first organ area and 200 total electrical potentials are sensed for a second organ area, at step 510, then the two sets of numbers may be normalized. For example, each electrical potential for the first organ area may be applied twice, such that the total number of electrical potentials for both the first organ area and the second organ area is 200.

The display of a rendering of the organ including the visual characteristics, per step 540 of the process illustrated in FIG. 5, may provide an identification of an outlier electrical potential area of the organ. The outlier electrical potential area of the organ may be an area with one or more organ areas associated with an outlier specific visual characteristic (e.g., purple) and, thus, exhibit a given outlier number of peak electrical potentials. For example, an outlying area of the organ may be an area that is colored purple, which corresponds to organ area(s) with greater than 200 peak electrical potentials. Such an outlier area may be identified as a potential source of unwanted electrical activity, such as that electrical activity that results in unwanted medical conditions including atrial fibrillation, tachycardia, etc. At step 550 of the process illustrated in FIG. 5, an ablation procedure may be performed such that a medical probe is used to ablate along an ablation area defined, at least in part, by the boundaries of or area occupied by visual characteristic. For example, the boundary defined by area 630 of FIG. 6 may be ablated at ablation points 640 such that electrical activity is no longer generated from within the area 630 as the tissue at the boundary defined by area 630 may be destroyed as a result of the ablation points 640.

Figure 7:
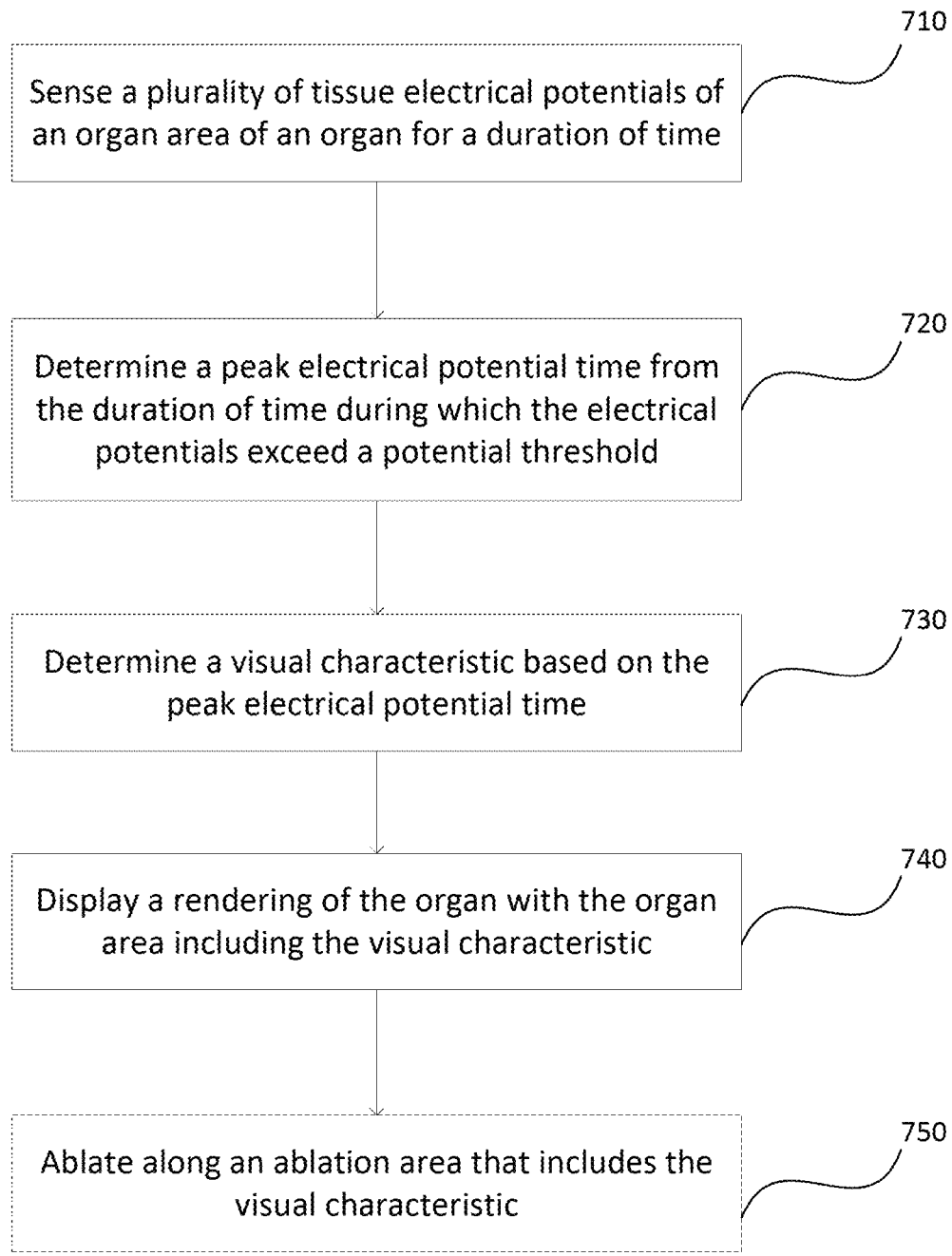
FIG. 7 is a flowchart for visualizing electrical potential activity based on time, in accordance with an embodiment of the disclosed subject matter.

As disclosed, FIG. 5 outlines displaying organ areas using visual characteristics, as determined based on the number of peak electrical potentials that exceed a potential threshold for a given organ area. FIG. 7 outlines a process 700 for displaying organ areas using visual characteristics, as determined based on an amount of time that the organ area exhibits electrical potentials greater than a potential threshold.

At step 710 of the process illustrated in FIG. 7, a plurality of tissue electrical potentials of an organ area are sensed for a duration of time. The plurality of electrical potentials may be sensed using a medical probe, such as medical probe 22 of FIG. 2A. The plurality of electrical potentials may be sensed by one or more electrodes of the medical probe as the medical probe traverses different organ areas of an organ, such as organ 401 of FIG. 4.

A medical probe may sense electrical potentials for each organ area for a duration of time. The duration of time for which electrical potentials are sensed per organ area may be pre-determined. According to an exemplary implementation, the duration of time may be in the range of 2 s and 3 s, for example, 2.5 seconds per organ area. According to an implementation, the medical probe may sense the electrical potentials per organ area for the pre-determined amount of time starting when the medical probe is in contact with or proximate to the tissue of the organ area. Alternatively, the medial probe may sense the electrical potentials per organ area, for the pre-determined amount of time, after a stabilizing period, such as an amount of time allocated for the medical probe to stabilize.

As an example, medical probe 22 of FIG. 2A may be in contact with organ area 411 of FIG. 4. The medical probe 22 may sense the electrical potentials at organ area 411 for a sum of 2.5 seconds and may then move to a different organ area.

At step 720 of the process illustrated in FIG. 7, an electrical potential time may be determined for each organ area. The electrical potential time may be the amount of time that the sensed electrical potentials for a given organ area exceed a potential threshold. Notably, the electrical potential time will be no longer than the duration of time that the electrical potentials for an organ area are sensed. A potential threshold may be determined or provided in accordance with the techniques disclosed herein.

As an example of step 720 of the process illustrated in FIG. 7, medical probe 22 of FIG. 2A may be in contact with the organ area 411 of FIG. 4 for 2500 milliseconds. The potential threshold may be set to 0.05 mV. At step 720, of FIG. 7, it may be determined that for 1500 milliseconds, of the total 2500 milliseconds, the electrical potential at organ area 411 exceeds the potential threshold of 0.5 mV. Accordingly, the electrical potential time for organ area 411 would be 1500 milliseconds.

At step 730 of the process illustrated in FIG. 7 a visual characteristic, for an organ area, may be determined based on the electrical potential time for that organ area, as determined at step 720. According to an implementation, the visual characteristic may be determined based on the electrical potential time divided by the total duration of time that electrical potentials for the organ area are sensed. A visual characteristic may be a color, a texture, a pattern, a gradient, an indicator, a graphic, or the like. A visual characteristic may be determined, rendered, or otherwise incorporated for display in accordance with the techniques and implementations disclosed herein.

At step 740 of the process illustrated in FIG. 7, a rendering of an organ that includes one or more organ areas may be displayed such that each organ area is rendered using its corresponding visual characteristic, as determined at step 730 of the process illustrated in FIG. 7. Accordingly, organ areas with the same or similar electrical potential times may be rendered with the same or similar visual characteristic (e.g., may be the same color). Further, it may also be probable that different organ areas that are proximate to each other may have similar electrical potential times and, thus, may be rendered similarly. For example, a number of organ areas that are proximate to each other may have electrical potential times of less than 500 milliseconds. Accordingly, this number of organ areas may all be rendered as red. It will be understood that although electrical potential times are described herein, a visual characteristic and/or rendering may be based on a percentage derived based on electrical potential times such as by dividing an electrical potential time by the duration of time that electrical potentials are collected at an organ area.

FIG. 8 is a rendering of a heart 801 with pattern visual characteristics based on the electrical potential times of a plurality of organ areas, in accordance with step 740 of the process illustrated in FIG. 7. The organ areas towards the top of the heart 801, as it is visually oriented in FIG. 8, have between 0 and 1000 millisecond electrical potential times. This area is indicated as area 810. Accordingly, area 810 of the heart 801 is rendered with a diagonal line pattern which corresponds to electrical potential times of between 0 and 1000 milliseconds. It should be noted that area 810 may include one or a number of organ areas, as disclosed herein, which exhibited electrical potential times in the range of 0-1000 milliseconds. The organ areas towards the bottom of the heart 801, as it is visually oriented in FIG. 8, have electrical potential times between 1001 and 2000 milliseconds. This area is indicated as area 820. Accordingly, area 820 of the heart 801 is rendered with a horizontal line pattern which corresponds to electrical potential times of between 1001 and 2000 milliseconds. It should be noted that area 820 may include one or a number of organ areas, as disclosed herein, which exhibit electrical potential times of between 1001 and 2000 milliseconds. The organ areas towards the center of the heart 801, as it is visually oriented in FIG. 8, have over electrical potential times over 2000 milliseconds. This area is indicated as area 830. Accordingly, area 830 of the heart 801 is rendered with a horizontal line pattern which corresponds to electrical potential times over 2000 milliseconds. It should be noted that area 830 may include one or a number of organ areas, as disclosed herein, which exhibited electrical potential times over 2000 milliseconds. It will be understood that although ranges of milliseconds are disclosed herein, including FIG. 8, that a rendering, legend, or other visual manifestation may be provided based on the percentage of time that a given organ area exhibits electrical potential times from the duration of time that potentials are collected.

The display of a rendering of the organ including the visual characteristics, per step 740 of the process illustrated in FIG. 7, may provide an identification of an outlier electrical potential area of the organ. The outlier electrical potential area of the organ may be an area with one or more organ areas associated with an outlier specific visual characteristic (e.g., purple) and, thus, exhibit a given outlier number of electrical potential times. For example, an outlying area of the organ may be an area that is colored purple, which corresponds to organ area(s) with electrical potential times over 2000 milliseconds. Such an outlier area may be identified as a potential source of unwanted electrical activity, such as that electrical activity that results in unwanted medical conditions including atrial fibrillation, tachycardia, etc. At step 750 of the process illustrated in FIG. 7, an ablation procedure may be performed such that a medical probe is used to create ablation points 840 along an ablation area defined, at least in part, by the boundaries of or area occupied by visual characteristic. For example, the boundary defined by area 830 of FIG. 8 may be ablated such that electrical activity is no longer generated from within the area 830 as the tissue at the boundary defined by area 830 may be destroyed based on ablation points 840 created by an ablation catheter.

According to an exemplary implementation of the disclosed subject matter, an indication may be received and, based on the indication; either the rendering as described in FIG. 5 based on a number of peak electrical potentials or a rendering as described in FIG. 7 based on an electrical potential time, may be displayed. The indication may be based on a stored preference, determined based on a patient or another criterion, or may be provided by a user. For example, a surgeon may alternate between both views by providing an input via an electronic input device such as via control console 24.

Figure 9:
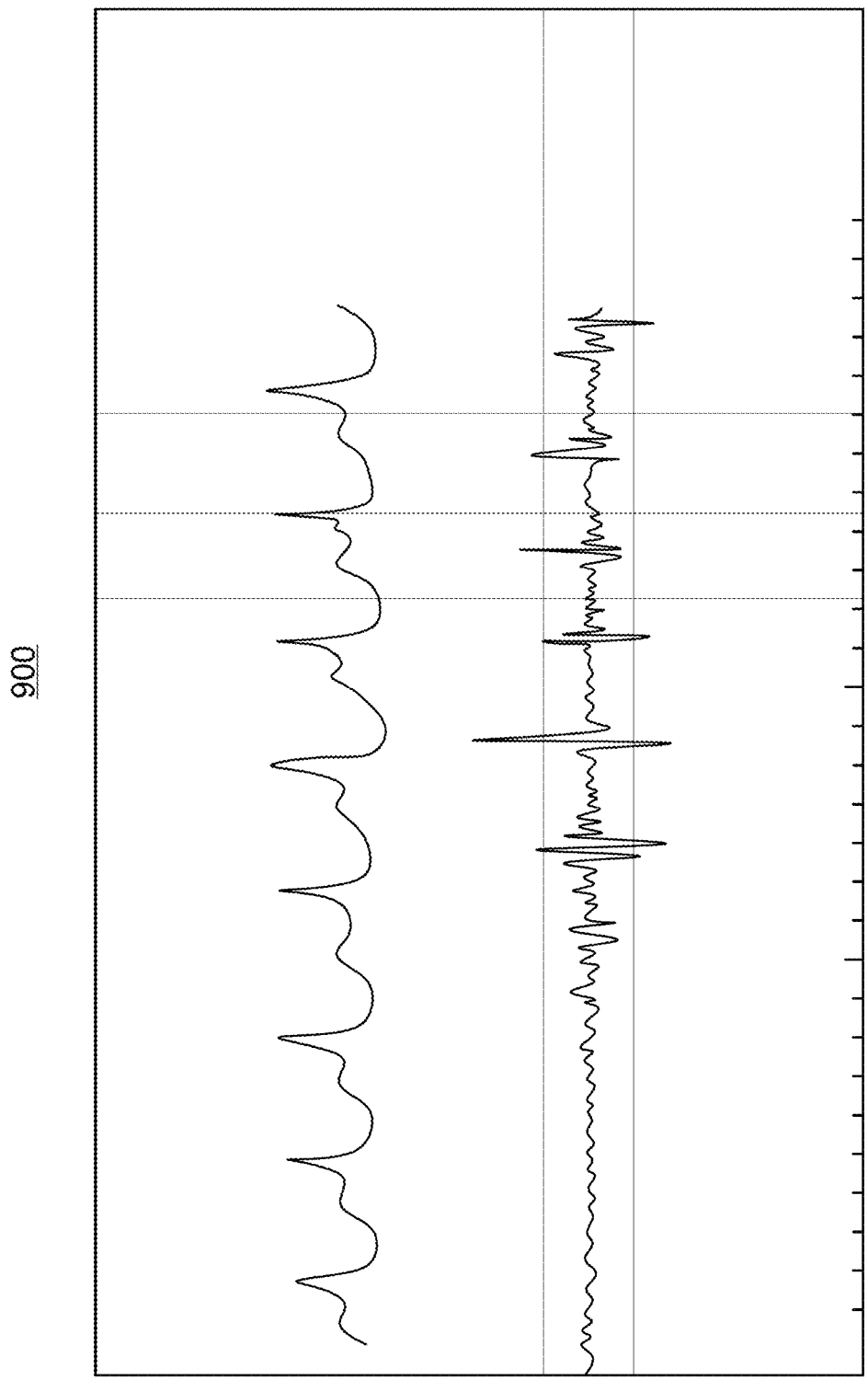
FIG. 9 is an image of an electrical potential signal response chart with a number of peaks and a lower percentage value.
Figure 10:
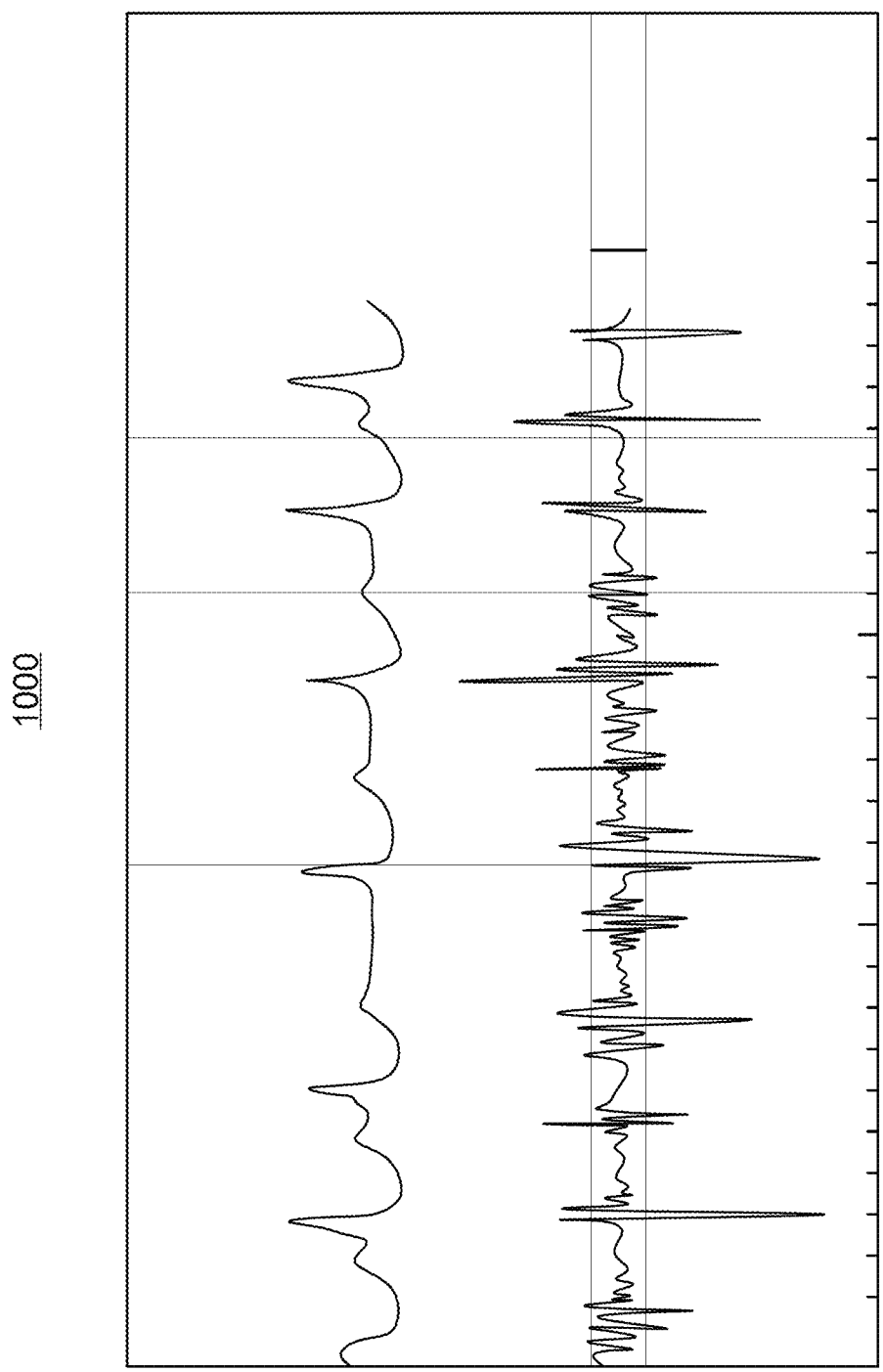
FIG. 10 is an image of an electrical potential signal response chart with a number of peaks and a higher percentage value.

FIG. 9 shows an image of an electrical potential signal response chart collected from a specific electrode. FIG. 9 shows a signal that includes 11 peaks corresponding to the process described in FIG. 5 and a lower percentage value, corresponding to the process described in FIG. 7. FIG. 10 shows another image of an electrical potential signal response chart collected from a specific electrode. FIG. 10 shows a signal that includes 108 peaks corresponding to the process described in FIG. 5 and a higher percentage value, corresponding to the process described in FIG.

According to an implementation of the disclosed subject matter, a scar area may be identified based on electrical potentials sensed by a medical probe. The electrical potentials may be sensed as described at step 510 of the process illustrated in FIG. 5 and/or step 710 of the process illustrated in FIG. 7.

A scar area may be identified based on the number of electrical potentials sensed at an organ area that are above a potential threshold, as disclosed herein, being below a scar threshold. For example, the scar threshold may be 500 electrical potentials above a potential threshold. Electrical potentials at an organ area may be sensed such that 2500 electrical potential readings are obtained. A determination may be made that only 400 of the 2500 electrical potential readings are above a potential threshold of 0.05 mV. Given that only 400 electrical potentials are above the potential threshold of 0.05 mV, it may be determined that the organ area is part of a scar area, as the 400 electrical potentials above the potential threshold is lower than the scar threshold of 500 electrical potentials above the potential threshold.

According to another implementation, a scar area may be identified based on the amount of time that sensed electrical potentials at an organ area is below a potential threshold, as disclosed herein, being below a scar time threshold. For example, the scar time threshold may be 500 milliseconds. Electrical potentials at an organ area may be sensed for 2500 milliseconds. A determination may be made that the sensed electrical potentials are above a potential threshold of 0.05 mV for only 400 of the 2500 milliseconds. Given that the sensed electrical potentials are above the potential threshold 0.05 mV for only 400 milliseconds, it may be determined that the organ area is part of a scar area, as the 400 milliseconds is lower than the scar time threshold of 500 milliseconds above the potential threshold.

A scar area visual characteristic may be determined for an organ area or group of organ areas identified as being part of a scar area. The visual characteristic may be different than the visual characteristics determined for organ areas that are not identified as scar areas (e.g., a scar area visual characteristic may be the color grey).

According to an implementation, a scar tissue may further be identified based at least in part on the shape of the surface area created by the organ areas identified as part of a scar area. According to this implementation, the shape of the surface area created by organ areas identified as being part of a potential scar area may be analyzed and compared to pre-determined criteria such that a surface area that matches one or more pre-determined criteria is designated a scar area.

According to an implementation of the disclosed subject matter, a complex fractionated atrial electrograms (CFAE) area may be identified based on electrical potentials sensed by a medical probe. The electrical potentials may be sensed as described at step 510 of the process illustrated in FIG. 5 and/or step 710 of the process illustrated in FIG. 7. A CFAE area may indicate fragmentation and may be an ideal area for ablation.

According to an exemplary implementation of the disclosed subject matter, the visual indications (e.g., raised bar) that dynamically show electrical potentials, as shown in FIG. 4, may be provided via a display on a rendering of an organ, such renderings shown in FIG. 6 and FIG. 8 (visual indications not shown in FIG. 6 and FIG. 8). The visual indications may be provided at the time of collection of the electrical potential activity or may be stored and provided at a subsequent time. For example, the medical probe 22 may be used to collect electrical potentials at different organ areas. These electrical potentials may be stored in memory, such as memory 56 of FIG. 2A. The electrical potentials may then be displayed at a later time by accessing the stored information in memory 56. Further, according to an implementation of the disclosed subject matter, such visual indicators may not be provided via a display. The electrical potentials may be utilized by processor 42 of FIG. 2A as they are collected or memory 56 may provide stored electrical potentials to processor 42. It should be noted that each organ area may have a number of corresponding sensed electrical potentials (e.g., 2500 sensed samples), as described herein. Accordingly, in order to view the electrical potentials of an organ area, a dynamic display may be provided and may cycle through the different sensed electrical potentials for each sensed organ area.

According to an exemplary embodiment of the invention, a given point on an organ may be rendered (e.g., colored, shaded, patterned, etc.) based on regional points. Notably, a given point may be rendered based on the peak values for the given point and/or peak values of neighboring points to the given point. The given point may be rendered using a visual characteristic that is determined based on a computation (e.g., average, median, mode, normalization, etc.) that factors in the peak values of neighboring points to the given point. By applying this regional points-based technique, a given point may be better represented in a rendering of an organ. Additionally, outlier peak values that may be anomalies and/or errors (e.g., due the movement of a probe, due to a faulty electrode, etc.) may be smoothed out based on implementing the regional points-based technique.

Figure 11:
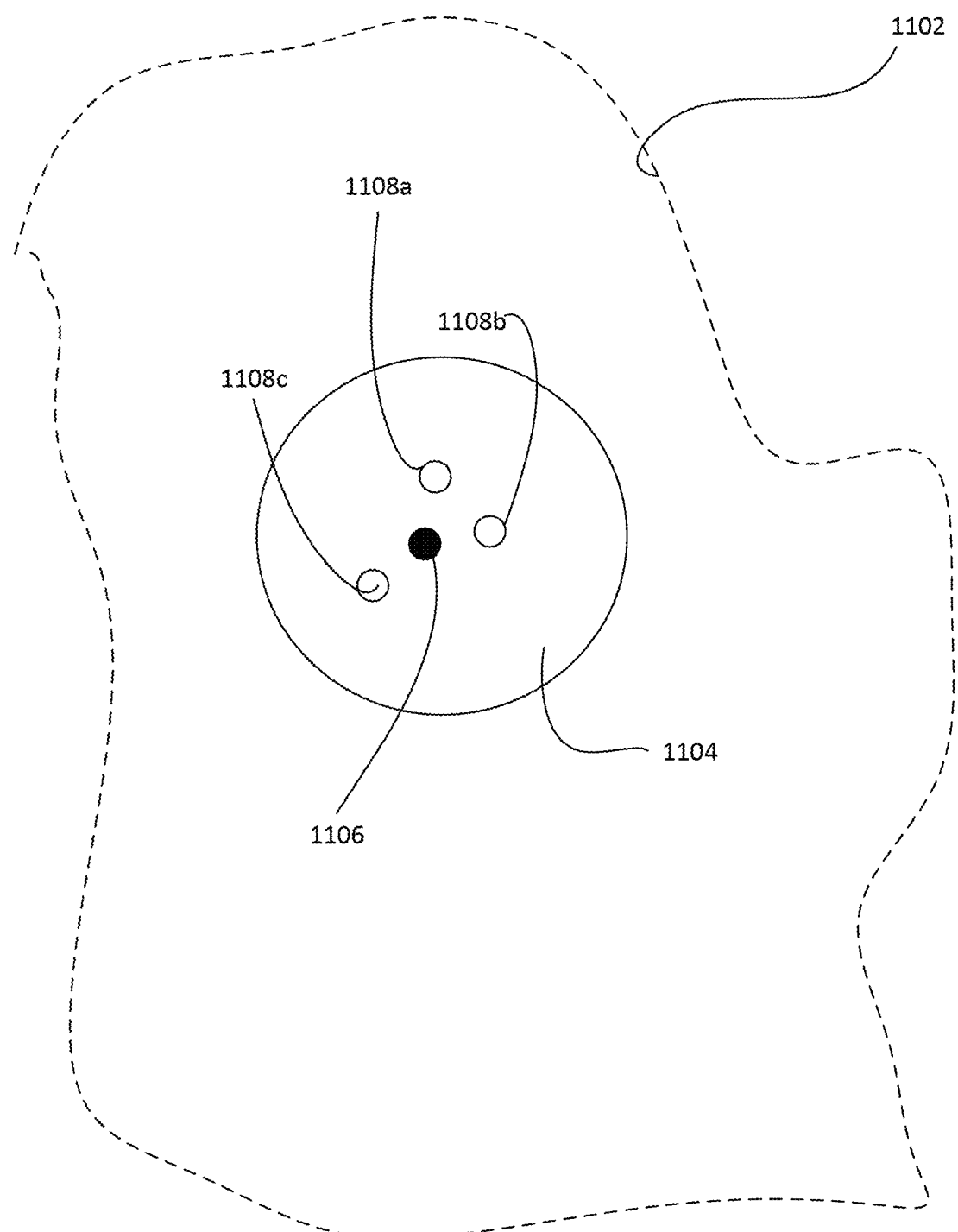
FIG. 11 is diagram of a regional potential map.

FIG. 11 shows an example embodiment of the regional points-based rendering, as disclosed herein. As shown in FIG. 11, an organ, such as heart 1102 may include a plurality of points. When determining rendering properties of given point 1106, a region 1104 (e.g., an area, a volume, a circle, a sphere, etc.) may be identified that may include the given point 1106. Additionally, the region 1104 may also include one or more additional points such as points 1108*a*, 1108*b*, and 1108*c*, as shown in FIG. 11. The additional points may be points for which electrical activity is available to the system. The number of points in the region and/or the dimensions or the region may be controlled using a graphical user interface or any other applicable control such as voice control, haptic feedback, etc.

As shown in FIG. 11, a region 1104 that is a subset of the organ 1102, may be determined either based on dimensions or based on the number of additional points to be included in the region 1104, as further disclosed herein. The given point 1106 may be the point to be rendered in accordance with the regional points-based rendering technique disclosed herein. The number of additional points 1108a, 1108b, and 1108c may be points that exhibit a minimum number of peaks of electrical signals, as measured, for example, by one or more electrodes. Each of the number of peaks of electrical signals may be peaks that exceed a minimum threshold value.

A visual indicator (e.g., color, shade, pattern, etc.) may be determined based on the result of a computation conducted based on the peaks exhibited by a given point and/or its neighboring point within a region (e.g., region 1104). Notably, the visual indicator may be based at least in part on the neighboring points rather then being based solely on the peaks exhibited by the given point alone. By incorporating the neighboring points in determining the visual indicator, the system may be able to render a more reliable image of an organ such that outlying or erroneous peaks are not exhibited within the rendering.

In the example shown in FIG. 11, the given point 1106 may exhibit 1400 peaks within a given time window. During the same time window, additional point 1108a may exhibit 1350 peaks, additional point 1108b may exhibit 1360 peaks, and additional point 1108c may exhibit 1370 peaks. A median value computation may be performed such that a median value of peaks for all associated points (i.e., given point 1106 and additional points 1108a, 1108b, and 1108c) is calculated as 1365 (i.e., the value between 1160 and 1170). Accordingly, the given point 1106 may be rendered based on the median value calculated as 1365 rather then the 1400 peaks exhibited by the given point 1106.

According to an exemplary embodiment of the invention, the dimensions (e.g., volume, area, size, etc.) of the region 1104 may be determined by a user, may be pre-determined, or may be determined dynamically.

A user may determine the dimensions of the region 1104 in any applicable manner such as by inputting a dimension (e.g., a radius). For example, a user may use a keyboard to select one or more keys which toggle the dimensions of the region 1104 surround a given point 1106. For example, the user may select the one or more keys to alternate between a radius of 0.5 mm, 1 mm, 1.5 mm, 2 mm, 2.5 mm, 3 mm . . . 10 mm, and back to 0.5 mm.

According to an exemplary embodiment of the invention, a user may input a visually guided dimension using an applicable input device. For example, a user may use a computer mouse, mousepad, or stylist type device to input the dimensions of the region 1104.

Pre-determined dimensions may be stored in a memory or may be default dimensions that are pre-programmed into a system to designate the size of a region 1104. Additionally, a system may dynamically determine the dimension for a region 1104 based on any applicable criteria such as, for example, a distance between a given point 1106 and neighboring points, a desired normalization amount, a type of medical condition, patient history, or the like.

According to an exemplary embodiment of the invention, a region 1104 may be defined based on a number of points to be included in the region. The number of points may be provided by a user, may be pre-determined, or may be dynamically determined.

A user may determine the number of points to be included in region 1104 in any applicable manner such as by inputting a number of points. For example, a user may use a keyboard or other input device to provide a number of points that surround a given point 1106, to be included in region 1104. For example, the user may provide any number of points such as 3 points, 10 points, 100 points, or the like.

Pre-determined number of points may be stored in a memory or may be a default number of points that are pre-programmed into a system. Additionally, a system may dynamically determine the number of points for a region 1104 based on any applicable criteria such as, for example, the number of peaks exhibited by a given point 1106, a desired normalization amount, a type of medical condition, patient history, or the like.

According to an exemplary embodiment of the invention, the regional points-based rendering, as disclosed herein, may be applied to each given point (e.g., point 1106 of FIG. 11) that meets a minimum number of peaks within a time window (e.g., 2.5 seconds). Additionally, each additional point (e.g., points 1108a, 1108b, and 1108c) may be a point that also meets the minimum number of peaks within a time window (e.g., 2.5 seconds).

Figure 12:
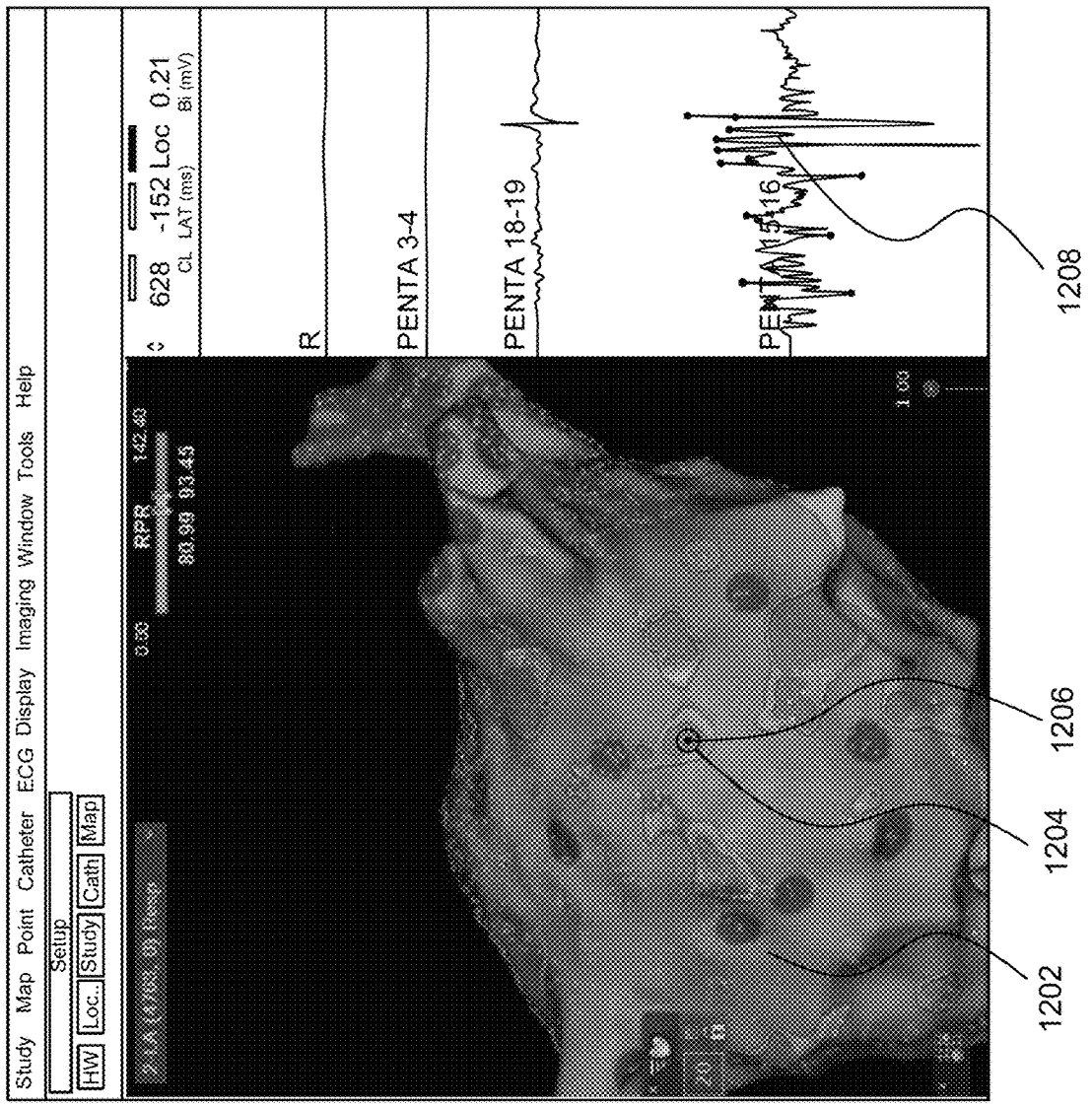
FIG. 12 is an image of a heart with visual characteristics for electrical potential activity based on a regional potential map.

FIG. 12 shows an image 1200 of a heart 1202 rendering with visual characteristics for electrical potential activity based on regional potential map. As shown in FIG. 12, visual indicators may be used to provide electrical activity information of the heart 1202. To determine the visual indicator (e.g., color in this example) for point 1206, a region 1204 may be identified. The visual indicator may be identified in part based on the number of peak values 1208 exhibited at point 1206, within a given time period. Additionally, the number of peak values for one or more additional points neighboring point 1206 may be identified. A computation based on the number of peak values at point 1206 as well as the number of peak values at the neighboring points may be implemented to generate a computed peak value number. The visual indicator may be determined based on this computed peak value number rather than the peak value number of the point itself. The visual indicator in this example may be red, to indicate the computed peak values corresponding to the value indicated by the visual indicator red.

Any of the functions and methods described herein can be implemented in a general-purpose computer, a processor, or a processor core. Suitable processors include, by way of example, a general-purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be mask works that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random-access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A method comprising:
sensing a plurality of first tissue electrical potentials at a first organ area of an organ, by one or more electrodes on a catheter;
determining a number of first peak electrical potentials from the plurality of first tissue electrical potentials wherein the number of first peak electrical potentials includes at least a subset of the plurality of first tissue electrical potentials that exceed a potential threshold;
determining a first visual characteristic based on the number of first peak electrical potentials;
determining a scar area by at least using the number of first peak electrical potentials to determine a number of electrical potentials that are greater than the potential threshold and less than a scar threshold;
determining a third visual characteristic based on the scar area; and
displaying a rendering of the organ comprising the first organ area such that the rendering of the first organ area comprises the first visual characteristic, and the third visual characteristic.

2. The method of claim 1, wherein the first visual characteristic is selected from one of a color, a texture, a pattern, a gradient, an indicator, and a graphic.

3. The method of claim 1, wherein the first visual characteristic is determined based on predetermined ranges.

4. The method of claim 1, further comprising:
sensing a plurality of second tissue electrical potentials at a second organ area of the organ, by the one or more electrodes on the catheter;
determining a number of second peak electrical potentials from the plurality of second tissue electrical potentials such that a second peak electrical potential exceeds the potential threshold;
determining a second visual characteristic based on the number of second peak electrical potentials; and
displaying the rendering of the organ comprising the second organ area such that the rendering of the second organ area comprises the second visual characteristic.

5. The method of claim 4, wherein the first visual characteristic is a first color and the second visual characteristic is a second color.

6. The method of claim 4, wherein the first visual characteristic is based on a ratio between the number of first peak electrical potentials and the number of second peak electrical potentials.

7. The method of claim 4, wherein a count of the plurality of first tissue electrical potentials and a count of the plurality of second tissue electrical potentials is the same.

8. The method of claim 4, wherein a first duration of time spent sensing the plurality of first tissue electrical potentials is the same as a second duration of time spent sensing the second tissue electrical potentials.

9. The method of claim 1, wherein determining the first visual characteristic is further based on one or more neighboring peak electrical potentials.

10. The method of claim 9, wherein the one or more neighboring peak electrical potentials corresponds to one or more neighboring points within a region surrounding the first organ area.

11. A method comprising:
sensing, for a first duration of time, a plurality of first tissue electrical potentials at a first organ area of an organ, by one or more electrodes on a catheter;
determining a first electrical potential time, such that the first electrical potential time is a subset of time of the first duration of time, that the first tissue electrical potentials exceed an electrical potential threshold;
determining a first visual characteristic based on the first electrical potential time;
determining a scar area from at least the first electrical potential time to determine a number of electrical potentials that are greater than the electrical potential threshold and less than a scar time threshold;
determining a third visual characteristic based on the scar area; and
displaying a rendering of the organ comprising the first organ area such that the rendering of the first organ area comprises the first visual characteristic, and the third visual characteristic.

12. The method of claim 11, wherein the first visual characteristic is selected from one of a color, a texture, a pattern, a gradient, an indicator, and a graphic.

13. The method of claim 11, wherein the first visual characteristic is determined based on predetermined time ranges.

14. The method of claim 11, further comprising:
sensing, for a second duration of time, a plurality of second tissue electrical potentials at a second organ area of the organ, by the one or more electrodes on the catheter;
determining a second electrical potential time, such that the second electrical potential time is a subset of time, from the second duration of time, that the second tissue electrical potential exceeds the potential threshold;
determining a second visual characteristic based on the second electrical potential time; and
displaying the rendering of the organ comprising the second organ area such that the rendering of the second organ area comprises the second visual characteristic.

15. The method of claim 14, wherein the first visual characteristic is based on a ratio between the first electrical potential time and the second electrical potential time.

16. The method of claim 14, wherein the first visual characteristic is further based on the electrical potential time divided by the first duration of time.

17. The method of claim 11, wherein determining the first visual characteristic is further based on one or more neighboring peak electrical potentials.

18. A system comprising:
a catheter comprising one or more electrodes and configured to sense a plurality of first tissue electrical potentials at a first organ area of an organ;
a processor configured to:
receive the plurality of first tissue electrical potentials;
determine a number of first electrical potentials from the plurality of first tissue electrical potentials such that the number of first peak electrical potentials includes at least a subset of the plurality of first tissue electrical potentials that exceed a potential threshold;
determine a first visual characteristic based on the number of first electrical potentials;
determine a scar area by at least using the number of first peak electrical potentials to determine a number of electrical potentials that are greater than the potential threshold and less than a scar threshold;

determine a third visual characteristic based on the scar area; and a display configured to render the organ comprising the first organ area such that the render of the first organ area comprises the first visual characteristic, and the third visual characteristic.

19. The system of claim 18 wherein the display is at least one of a television, monitor, mobile device, and hologram.

20. The system of claim 18, wherein the catheter is one of a single electrode and a multi electrode catheter.

* * * * *

UNITED STATES PATENT AND TRADEMARK OFFICE
CERTIFICATE OF CORRECTION

PATENT NO. : 11,844,616 B2
APPLICATION NO. : 16/986871
DATED : December 19, 2023
INVENTOR(S) : Refael Itah et al.

It is certified that error appears in the above-identified patent and that said Letters Patent is hereby corrected as shown below:

On the Title Page

In Item (57), under "ABSTRACT", in Column 2, Line 6, delete "the a" and insert -- the --, therefor.

In the Specification

In Column 1, Line 34, delete "to hospital" and insert -- to hospital. --, therefor.

In Column 2, Line 19, delete "diagram" and insert -- a diagram --, therefor.

In Column 3, Line 3, delete "on" and insert -- upon --, therefor.

In Column 3, Line 5, delete "combing" and insert -- combining --, therefor.

In Column 3, Line 43, delete "server a" and insert -- server by a --, therefor.

In Column 7, Line 55, delete "minimum" and insert -- a minimum --, therefor.

In Column 12, Line 29, delete "over electrical" and insert -- electrical --, therefor.

In Column 13, Line 19, delete "FIG." and insert -- FIG. 7 --, therefor.

In Column 14, Line 46, delete "due" and insert -- due to --, therefor.

In Column 14, Line 60, delete "or" and insert -- of --, therefor.

In Column 15, Line 13, delete "then" and insert -- than --, therefor.

In Column 15, Line 29, delete "then" and insert -- than --, therefor.

Signed and Sealed this
Eleventh Day of June, 2024

*Katherine Kelly Vidal*

Katherine Kelly Vidal
*Director of the United States Patent and Trademark Office*

CERTIFICATE OF CORRECTION (continued)
U.S. Pat. No. 11,844,616 B2

In Column 15, Line 39, delete "surround" and insert -- surrounding --, therefor.

In the Claims

In Column 19, Line 7, in Claim 19, delete "claim 18" and insert -- claim 18, --, therefor.

In Column 19, Line 10, in Claim 20, delete "multi electrode" and insert -- multi-electrode --, therefor.